(12) United States Patent
Izeki et al.

(10) Patent No.: US 6,231,858 B1
(45) Date of Patent: *May 15, 2001

(54) BOLUS FOR RADIOTHERAPY

(75) Inventors: Shin Izeki; Kazunori Hatakeyama; Fumitaka Ebihara; Yoshinori Koga, all of Kawaguchi (JP)

(73) Assignee: Mochida Corporation, Saitama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/158,580

(22) Filed: Sep. 22, 1998

(30) Foreign Application Priority Data

Jan. 9, 1998 (JP) ................................. 10-013474

(51) Int. Cl.⁷ .................................................. A61K 39/40
(52) U.S. Cl. ........................................................ 424/169
(58) Field of Search ............................... 127/34; 536/114, 536/102, 3, 112, 2; 106/145.1, 145.2, 144.1, 138.1, 160.1; 527/300; 424/1.11, 1.65, 1.69, 9.1, 1.73; 530/354

(56) References Cited

U.S. PATENT DOCUMENTS

| 3,865,603 | * | 2/1975 | Szymanski et al. | 106/130 |
| 4,130,555 | * | 12/1978 | Ohtsuka et al. | 260/117 |
| 4,500,358 | * | 2/1985 | Mayer et al. | 106/122 |
| 4,517,216 | * | 5/1985 | Shim | 426/573 |
| 5,126,328 | * | 6/1992 | Bower et al. | 514/21 |

FOREIGN PATENT DOCUMENTS

| 195 38 015 A1 | 3/1997 | (DE) . |
| 0211482 A2 | 2/1987 | (EP) . |
| 60-199835 | 10/1985 | (JP) . |
| 62-204770 | 9/1987 | (JP) . |

OTHER PUBLICATIONS

Ito et al, Radioisotopes, vol. 47, pp. 19–28, States of Water Molecules of Hydro Geiseidadated from 0–Positronium Lifetime measurement (English translation) Jan. 1998.*
Matsubashi et al, Food Irradiat. Jpn, vol. 21, No. 1–2, pp. 29–42, Effects of Gamma Irradiation on Melting Point of Gel of Agar & Carrageenan (English translation) 1986.*
Matsuhashi et al (1986), Food Irradiat. Jpn., 21 (1–2), 29–42, "Effects of Gamma Irradiation on Melting Point of Gel of Agar and Carrageenan." .*
Ito et al (Jan., 1998), Radioisotopes, vol. 47, No. 1, pp. 19–28, "States of water molecules of hydro gels elucidated from 0–positronium".*
Singh et al (1980), J. of Scientific and Industrial research, vol. 39, pp. 162–171, "Polymeric Hydrogels: Preparation and Biomedical Applications".*
Nakamura (1998), Res. Rep. Fac. Eng., Mie Univ, 23, 149–150, "Studieson Functional Hydro–Gels Preparation and its Characterization in the course of volume Phase transition."*
Collett et al (1980 (RECD 1981)), J. Pharm. Pharmacol. 32 (suppl), 6P, "The Effects of Some Solutes on the Hydration of Poly (HEMA) Hydrogels Prepared by Chemical of Radiation procedures".*

* cited by examiner

*Primary Examiner*—Dameron L. Jones
(74) *Attorney, Agent, or Firm*—Birch, Stewart, Kolasch & Birch, LLP

(57) ABSTRACT

A process for producing boluses for radiotherapy, which are disposable and excellent in processability. Natural organic polymers used as gelatinization preparations are added in water not higher than 10%, and more preferably 2–5% of water in order to produce a hydro gel comprising natural organic polymers. Then, the boluses which have equivalent to human body and are inexpensive, disposable, and excellent in processability can be obtained.

13 Claims, 5 Drawing Sheets

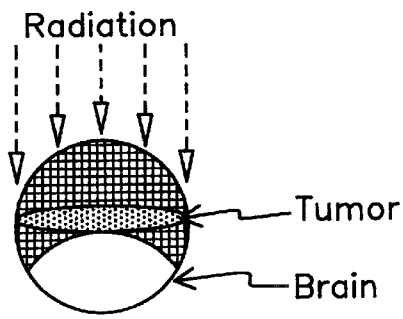
FIG.3A
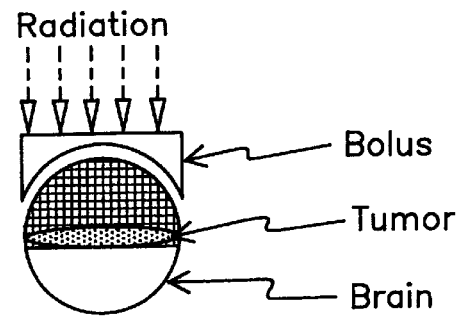
FIG.3B
FIG.4
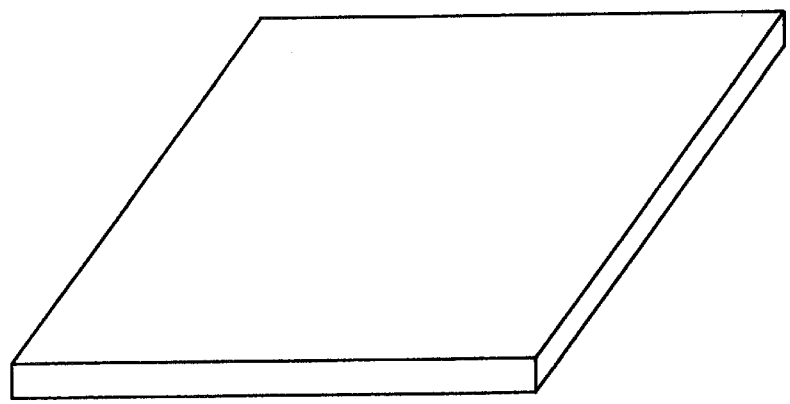

BOLUS FOR RADIOTHERAPY

BACKGROUND OF THE INVENTION

1. Field of the Invention

The present invention relates to a bolus used closely contacting with a human body to correct distribution of absorbed dose in radiotherapy, and particularly to a disposable bolus.

2. Description of the Prior Art

Irradiation of rays such as X-rays, γ-rays, and electron rays to a human body has been widely used for therapy against disease such as cancer. When the rays are irradiated on material, generally, dose of the rays decreases with depth, but the dose of the scattering rays whose directions are various increases. Therefore, the dose distribution of rays decreases exponentially with depth as shown in FIG. 6 and FIG. 7. But in rays with high energy the recoiling electrons and/or scattering rays have the components of forward direction mainly, and side scattering rays decrease. Therefore, the dose of rays becomes the greatest at a certain depth compared with surface dose, and after that the dose of rays decreases exponentially with depth as shown in FIG. 6 and FIG. 7. In therapy to treat the effect of these rays on human skin, the therapy sometimes causes adverse effects because of irradiation of unnecessary rays to normal tissues other than lesions.

For example, assuming that there is a focus under the skin surface in the position of 5 mm as shown in FIG. 1. If rays whose absorbed dose serves as the maximum under the skin surface in the position of 10 mm are irradiated to this focus to cure the focus, the unnecessary and excess rays are irradiated to normal tissues other than the focus. Especially, in the position of 10 mm under the skin surface the absorbed dose is the greatest, therefore it is risky to cause this part to accompany radiation damage. The bolus has a function to control the dose distribution of rays to irradiate the greatest absorbed dose to the focus. The bolus is used by making it intervene between an irradiation apparatus and a human body as shown in FIG. 2. Using a bolus as mentioned above, it is possible to cure lesions by irradiating a required therapeutic dose of rays to lesions efficiently.

If radiotherapy is performed to a tumor in the brain as shown in FIG. 3A, the dose distribution of rays in the brain is a spherical distribution reflecting an outward form of a head. In this situation, the dose distribution of the greatest absorbed dose is also a spherical distribution to the tumor which have a plate-like form as shown in FIG. 3A. Therefore, it is very dangerous that the greatest absorbed dose is irradiated to a part except the tumor as shown in FIG. 1. Here using the bolus which has a form fitted to an outward form of a head as shown in FIG. 3B, it is possible to correct the spherical distribution of rays.

Generally, a practically usable bolus must satisfy at least the following properties and conditions:

1. It is a substance equivalent to human body tissue.
2. It is homogeneous.
3. It has excellent plasticity, appropriate resilience, and excellent form-compatibility and adhesiveness to a living body.
4. It is non-toxic.
5. There are no changes in energy, etc.
6. It has even thickness.
7. It does not contain air.

Moreover, it is desirable to have the transparency in addition to the above properties and conditions. Although the expression "equivalent to human body tissue" means in a strict manner that the atomic composition is the same as that of a human body, it means in this context that properties in terms of absorption and scattering of rays are the same as those of substantial tissue.

Plastics, paraffin, synthetic rubbers, silicone, water, and the like have been used as bolus materials up to date.

SUMMARY OF THE INVENTION

Recently, since bacterial and viral infections in the hospital via medical apparatus and instruments have become a serious problem and in light of HIV infection, a demand for disposable instruments that are disposed after having been used only once has been further increasing.

However, since the price of conventional boluses using plastics, paraffin, silicone, or synthetic rubbers as their base material is very expensive and although the boluses are based on the size, and they must be disposed of as so-called industrial wastes because the used boluses can not be disposed of easily without treatment. Therefore, it is unrealistic to dispose the boluses after only one use.

Using the above-mentioned boluses, there are problems with respect to time and costs, because the boluses according to the prior art technology had to be used repeatedly and the boluses must be disinfected to maintain cleanliness before reuse. Moreover, repeated use may give an uncomfortable feeling to persons undergoing diagnosis in terms of cleanliness.

When water is used as bolus, although water itself can be easily disposed, containers enclosing water can not be easily disposed. In addition, there is a problem in the manufacturing technique that makes it difficult to enclose water.

The object of the present invention is to provide a bolus that satisfies various properties required for a bolus, and is disposable, can be prepared more inexpensively than conventional ones, and is excellent in terms of cleanliness and processability to solve the above-mentioned problems.

An invention of this application relates to preparation method of boluses for radiotherapy, which are inexpensive, disposable, and excellent in terms of processability, and the above objects in this invention are achieved with hydro gels using specific natural organic polymer gelatinizing preparations

BRIEF DESCRIPTION OF THE DRAWINGS

FIGS. 3A and 3B are illustrations showing the difference in the dose distribution of rays with and without a bolus in radiotherapy at the head.

FIG. 4 is a general view showing one example of a bolus in this invention.

DESCRIPTION OF THE PREFERRED EMBODIMENTS

A bolus of the present invention has a form of a rectangular plate and is composed of a hydro gel comprising natural organic polymer substances. Desirably, natural organic polymer gelatinizing preparations used in the present invention have strength and water-retentivity sufficient for practical use and can produce hydro gels with a water content not lower than 80%.

Natural organic polymers such as carrageenan, locust bean gum, glucomannan, starch, curdlan, guar gum, agar, cassia gum, dextran, amylose, gelatin, pectin, xanthan gum, tara gum, and gellan gum are mentioned as such gelatinizing preparations.

When a hydro gel comprising natural organic polymer is prepared, one or more of these gelatinizing preparations can be used together.

The amounts of the gelatinizing preparations added may range from not lower than a concentration for gelatinization to a concentration not providing gel as hard as a bolus, and are preferably not higher than 10%, and more preferably 2–5% of water. But some natural organic polymer materials such as gellan gum and pectin in the above examples do not gelatinize by the above method. Therefore, it is possible to gelatinize adding metal salts of calcium, potassium, sodium, barium and so on, in the solution after the gelatinizing preparations have dissolved in the water and have been stirred. Also, it is possible to add the metal salts of calcium, potassium, sodium, barium and so on in the solution after the gelatinizing preparations are dissolved in water and are stirred in the use of easily gelatinized gelatinization preparations. The prepared hydro gel comprising natural organic polymer then becomes stronger than a hydro gel comprising natural organic polymer without metal salts in strength. Some natural organic polymers, such as pectin, gelatinize or do not gelatinize with the value of pH. Therefore, in order to adjust to pH conditions of the range which is easy to gelatinize, from the alkalinity and the acid conditions which are hard to gelatinize, a pH-controlling agent must be added. The pH-controlling agent has another function to stabilize gelatinized material over time. The pH-controlling agent can be added, after the gelatinizing preparations are dissolved in water are and stirred, the same as in the case of the addition of the metal salts. Although it is desirable for a bolus to be colorless and transparent, it is possible to add a coloring agent in order to have a colored, transparent bolus according to circumstances.

The method of manufacturing a bolus for radiotherapy according to the present invention is now illustrated using carrageenan and locust bean gum as examples.

Figure 1:
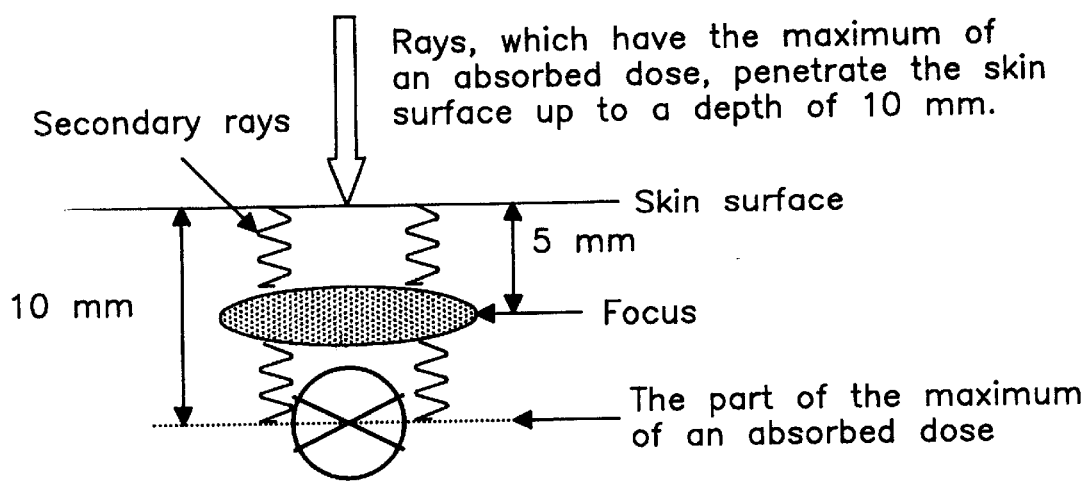
FIG. 1 is an illustration showing the relation between the intensity of radiation and the focus in the human body for radiotherapy.
Figure 2:
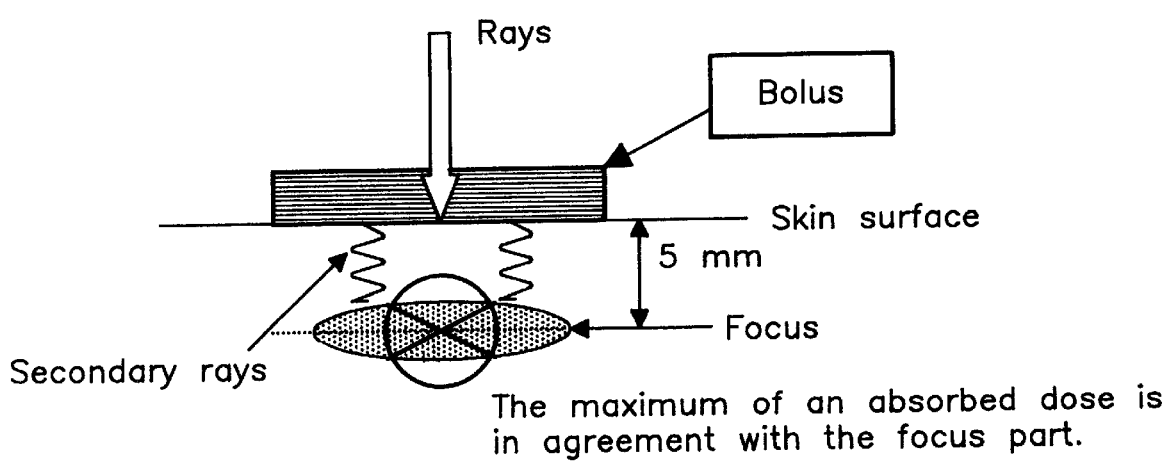
FIG. 2 is an illustration showing the relation between the intensity of radiation and the focus in the human body for radiotherapy in inserting bolus between source of radiation and the skin.
Figure 5A:
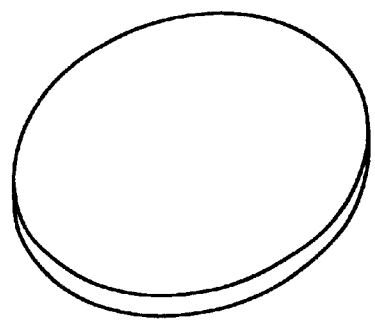
FIGS. 5A–5C are other examples in this invention.
Figure 5B:
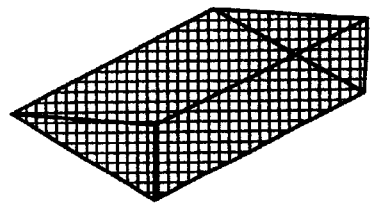
Figure 5C:
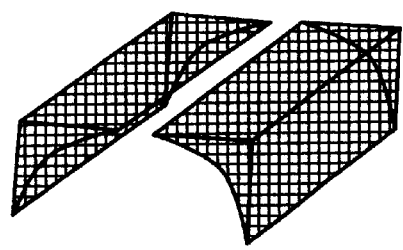

First, carrageenan and locust bean gum are dissolved in water by heating at 70–100° C., immediately poured in an appropriate mold, and cooled. Then, a bolus is obtained by gelatinizing it. The strength and feeling of hardness of the gel can vary over a wide range by selecting types and amounts of gelatinizing preparations. The size of the gel can also be changed according to the selection of the mold, without being limited to the form of FIG. 4, circular which is shown in FIG. 5A or triangular which is shown in FIG. 5 B form is sufficient, and that which carried out in a complicated form as shown in FIG. 5C is sufficient, and there may be other forms. Also, the size of even molded gel can be freely changed, since the gel can be easily cut by such as a knife.

Since a hydro gel comprising natural organic polymers according to this invention can be easily molded and its size can be freely changed, various boluses for the difference in the kind of rays, the difference in the depth from the skin surface of lesions, and the difference in the human-body form by the difference in the part which medical treatment is performed can be easily prepared.

The present method has such a merit that homogenous gel can be obtained with no special required apparatuses or operation required, which is advantageous in terms of energy-saving and stabilization of product quality.

It is desirable to add preservatives and anti-mold agents in advance during manufacturing of hydro gel, since molds and bacteria may adhere and propagate when the hydro gel of the present invention is stored over a long time. These preservatives and anti-mold agents are added after the gelatinizing preparations are dissolved in water and are stirred up.

Since the hydro gel of the present invention is intended to be used as a bolus for radiotherapy, it must be avoided to contain air bubbles in the gel as thoroughly as possible. Large bubbles or a great number of bubbles may serve as a cause of change in their carry-over depth (range), when the gel is used in therapy with charged particles such as electron rays and proton rays.

The bolus for radiotherapy according to the present invention has no toxicity, appropriate flexibility and resiliency, and excellent adhesiveness to a living body, homogeneity of material, and equivalency to human body tissue. In addition, at radiotherapy, fitting to a skin mark is easy due to its transparency. Lamination of boluses for radiotherapy with various thicknesses enables easy control of dose distribution of rays. Therefore, the hydro gel of the present invention is suitable as material for boluses used in radiotherapy.

EXAMPLE

The example of preparation in a bolus for radiotherapy with 40 cm$^3$ in total volume is mentioned below. With respect to the mixture 390 grams of water, 4.0 grams of carrageenan, 3.0 grams of locust bean gum, and 3.0 grams of xanthan gum are added. The mixture was heated and stirred at 80° C. for 10 minutes to dissolve. Then all the solution was poured into a container of 200 mm in width, 200 mm in length, and 10 mm in depth with attention paid not to contain gas bubbles. The container was soaked in water at 5° C. to cool and solidify the solution to obtain hydro gel with a thickness of 10 mm. As a result, homogenous hydro gel with excellent transparency and plasticity and appropriate resiliency was obtained. The gel thus obtained had a specific gravity of 1.01 and hardness of 34 measured by Asker hardness meter FP.

In order to show that absorption or scattering of rays of the hydro gel obtained in the example exhibited properties the same as those of substantial tissue through evaluation, percentage depth dose curves were measured to X-rays and electron rays. X-rays with 4 MV and 10 MV are used, a distance from a generating focus to a surface of the bolus is 100 cm, and X-ray irradiation field is 10×10 cm$^2$. Electron rays with 6 MeV, 9 MeV, 12 MeV, 15 MeV, and 18 MeV are used, a distance from an injection window to a surface of the bolus is 100 cm, electron ray irradiation field is 15×15 cm$^2$. Measurements are performed by a UNIDOS dose meter (manufactured by PTW) according to the standard measurement method.

Clinac CL-2100C (manufactured by VARIAN) was used for generation of X-rays and electron rays. JARP type, Markus type (manufactured by PTW) was used as an ionization box and RW3 (manufactured by PTW) was used as a phantom for measurement of absorbed dose in measurement. The phantom used here is composed of a substance whose interaction with rays such as absorption and scattering equivalent to that of human body tissue and whose density is as close as possible to that of human body tissue (substance equivalent to tissue), the same as a bolus.

Figure 6:
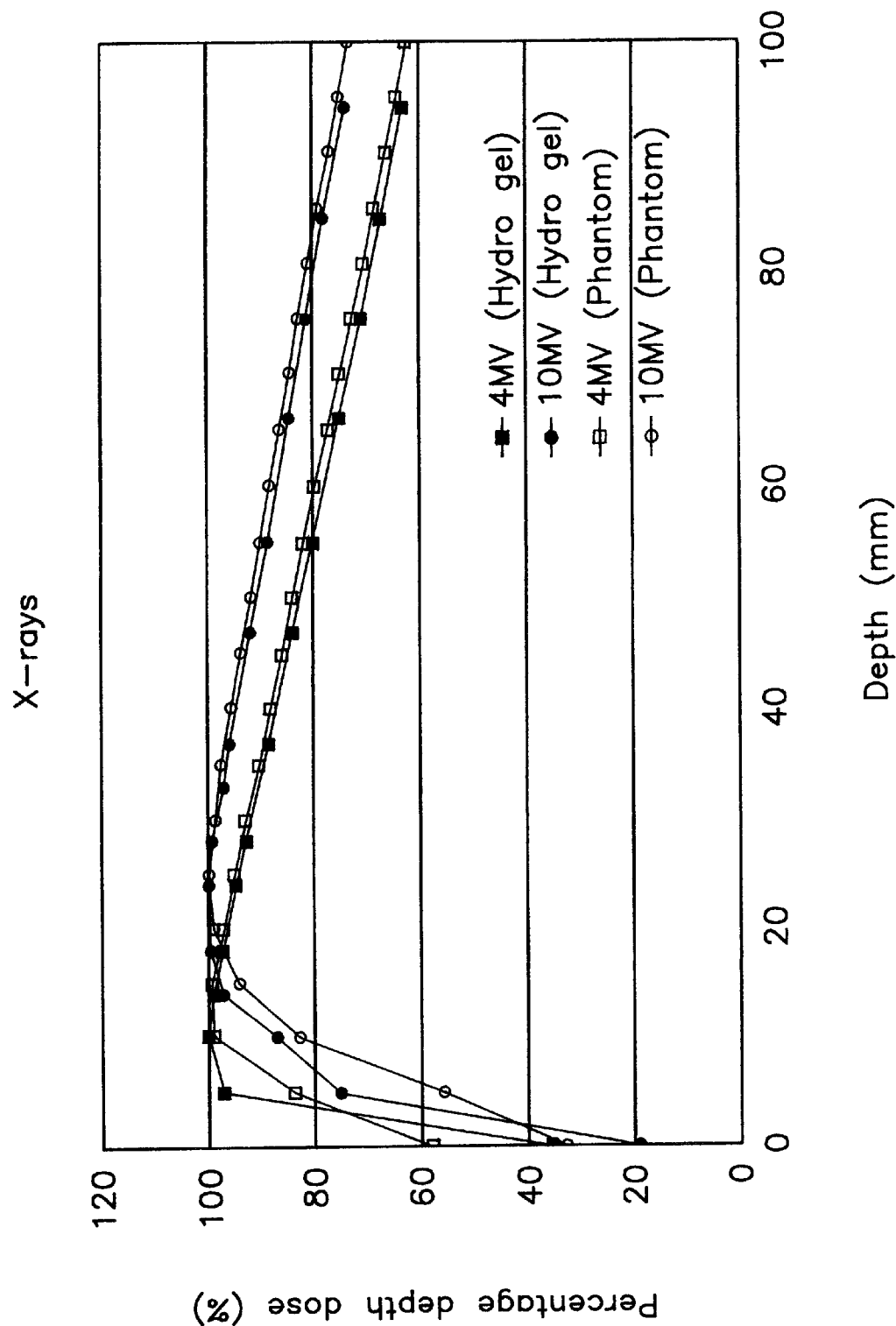
FIG. 6 is a graph showing the relation between the depth and percentage depth dose for X-rays of the bolus of the present invention.

FIG. 6 shows the percentage depth dose curves of the hydro gel and the phantom for X-rays of 4 MV and 10 MV. Since it is indicated that the percentage depth dose curves of the hydro gel are almost equal to those of the phantom at all depths, the hydro gel is high equivalent to that of human body tissue for X-rays.

Figure 7:
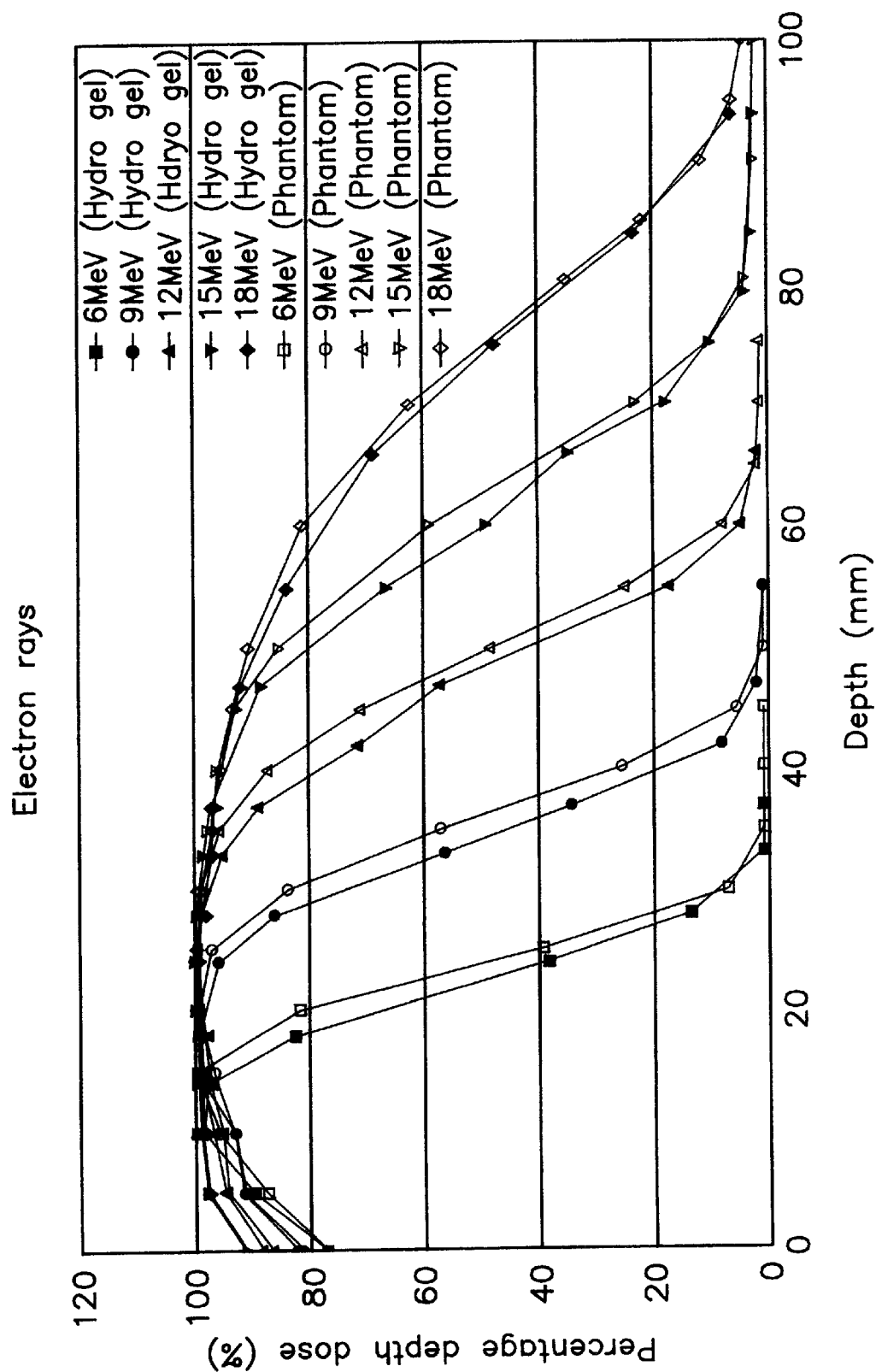
FIG. 7 is a graph showing the relation between the depth and percentage depth dose for electron rays of the bolus of the present invention.

FIG. 7 shows the percentage depth dose curves of the hydro gel and the phantom for electron rays of 6 MeV, 9 MeV, 12 MeV, 15 MeV, and 18 MeV. Since it is indicated that the percentage depth dose curves of the hydro gel are almost equal to those of the phantom at all depths, the hydro gel is high equivalent to that of human body tissue for electron rays.

From the above, the bolus of the present invention can achieve absorption of rays similar to that of the phantom. In other words, it can be understood that the bolus of the present invention is highly equivalent to human body tissue and very useful as a bolus for radiotherapy.

The example above serves only as an example and, of course, does not limit the scope of the present invention.

What is claimed is:

1. A method for using a bolus in radiotherapy, comprising contacting with a human body a bolus which is produced by adding a natural organic polymer, as a gelatinization preparation, in water at a concentration not higher than 10% water, wherein the natural organic polymer is at least one item selected from the group consisting of carrageenan, locust bean gum, glucomannan, starch, curdlan, guar gum, agar, cassia gum, dextran, amylose, gelatin, pectin, xanthan gum, tara gum, and gellan gum.

2. The method as claimed in claim 1, wherein a metal salt, a coloring agent, or a pH-controlling agent is added to the solution after the natural organic polymer, which is difficult to gelatinize, is heated and dissolved in water to make gelatinization easy.

3. The method as claimed in claim 1, wherein a metal salt is added in order to harden the bolus after the natural organic polymer, which is at least one item selected from the group consisting of carrageenan, locust bean gum, glucomannan, starch, curdlan, guar gum, agar, cassia gum, dextran, amylose, gelatin, pectin, xanthan gum, tara gum, and gellan gum, is heated and dissolved in water.

4. The method as claimed in claim 1, wherein a preservative is added after the natural organic polymer, which is at least one item selected from the group consisting of carrageenan, locust bean gum, glucomannan, starch, curdlan, guar gum, agar, cassia gum, dextran, amylose, gelatin, pectin, xanthan gum, tara gum, and gellan gum, is heated and dissolved in water.

5. The method as claimed in claim 1, wherein an anti-mold agent is added after the natural organic polymer, which is at least one item selected from the group consisting of carrageenan, locust bean gum, glucomannan, starch, curdlan, guar gum, agar, cassia gum, dextran, amylose, gelatin, pectin, xanthan gum, tara gum, and gellan gum, is heated and dissolved in water.

6. The method as claimed in claim 1, wherein the bolus is fabricated into a rectangular shape.

7. The method as claimed in claim 1, wherein the bolus is fabricated into a circular shape.

8. The method as claimed in claim 1, wherein the bolus is fabricated into the shape of a triangle pole.

9. The method as claimed in claim 1, wherein the bolus is fabricated into the shape of a human head.

10. A bolus for radiotherapy, characterized in that the bolus is produced by adding natural organic polymers, as a gelatinization preparation, in water at a concentration not higher than 10%, and wherein a metal salt is added to the solution after the natural organic polymers are heated and dissolved in water to strengthen the gel intensity, and wherein the natural organic polymer is at least one item selected from the group consisting of carrageenan, locust bean gum, glucomannan, starch, curdlan, guar gum, agar, cassia gum, dextran, amylose, gelatin, pectin, xanthan gum, tara gum, and gellan gum.

11. A bolus for radiotherapy as claimed in claim 10, wherein a pH-controlling agent is added to the solution simultaneously with a metal salt after the natural organic polymer is heated and dissolved in water, and wherein the addition of the pH-controlling agent aids in the gelatinization.

12. The bolus for radiotherapy according to claim 10, wherein the metal salt is a salt of calcium, potassium, sodium or barium.

13. The bolus for radiotherapy according to claim 11, wherein the metal salt is a salt of calcium, potassium, sodium or barium.

* * * * *